US012796973B2

(12) United States Patent
Kang et al.

(10) Patent No.: US 12,796,973 B2
(45) Date of Patent: Nov. 17, 2026

(54) CALIBRATION ALARM METHOD

(71) Applicant: I-SENS, INC., Seoul (KR)

(72) Inventors: Young Jea Kang, Seoul (KR); Ji Seon Nah, Seoul (KR); Min Ji Jang, Seoul (KR); Jung Hee Seo, Seoul (KR); Yun Hee Kang, Seoul (KR)

(73) Assignee: I-SENS, INC., Seoul (KR)

( * ) Notice: Subject to any disclaimer, the term of this patent is extended or adjusted under 35 U.S.C. 154(b) by 275 days.

(21) Appl. No.: 18/693,132

(22) PCT Filed: Jun. 2, 2022

(86) PCT No.: PCT/KR2022/007878
§ 371 (c)(1),
(2) Date: Mar. 18, 2024

(87) PCT Pub. No.: WO2023/128082
PCT Pub. Date: Jul. 6, 2023

(65) Prior Publication Data

US 2024/0382115 A1 Nov. 21, 2024

(30) Foreign Application Priority Data

Dec. 31, 2021 (KR) ........................ 10-2021-0194270

(51) Int. Cl.
*A61B 5/145* (2006.01)
*A61B 5/00* (2006.01)

(52) U.S. Cl.
CPC ...... *A61B 5/14532* (2013.01); *A61B 5/14503* (2013.01); *A61B 5/7435* (2013.01);
(Continued)

(58) Field of Classification Search
CPC .............. A61B 5/1495; A61B 5/14532; A61B 5/14503; A61B 5/74
See application file for complete search history.

(56) References Cited

U.S. PATENT DOCUMENTS 10,901,371 B2 * 1/2021 Vaissiere ................. G04F 13/00
2007/0208244 A1 9/2007 Brauher et al.
2010/0274515 A1 10/2010 Hoss et al.

FOREIGN PATENT DOCUMENTS

EP 2 256 494 1/2017
KR 10-0785065 12/2007
(Continued)

OTHER PUBLICATIONS

Extended European Search Report dated Jul. 16, 2025 for European Patent Application No. 22916237.5.
(Continued)

*Primary Examiner* — Eric F Winakur
(74) *Attorney, Agent, or Firm* — WOMBLE BOND DICKINSON (US) LLP

(57) ABSTRACT

The present invention relates to a method for providing a calibration alarm in a continuous biometric information measurement system, and more particularly, to a calibration alarm method, wherein the next calibration time is calculated on the basis of an actual calibration time of a user so that the next calibration time calculated on the basis of the actual calibration time can be notified to the user even if the calibration is performed differently from a preset calibration cycle, and contextual information of the user is considered and a calibration alarm is provided according to the contextual information of the user so that the user can conveniently input a reference biometric value.

10 Claims, 10 Drawing Sheets

(52) U.S. Cl.
CPC ................. *A61B 2560/0228* (2013.01); *A61B 2560/045* (2013.01); *A61B 2560/0462* (2013.01)

(56) References Cited

FOREIGN PATENT DOCUMENTS

| | | |
|---|---|---|
| KR | 10-2014-0016041 | 2/2014 |
| KR | 10-2021-0017482 | 2/2021 |
| KR | 10-2021-0064651 | 6/2021 |
| KR | 10-2021-0115574 | 9/2021 |

OTHER PUBLICATIONS

International Search Report for PCT/KR2022/007878 mailed on Apr. 3, 2023 and its English translation from WIPO (now published as WO 2023/128082).

Written Opinion of the International Searching Authority for PCT/KR2022/007878 mailed on Apr. 3, 2023 and its English translation from WIPO (now published as WO 2023/128082).

* cited by examiner

[Fig. 1]
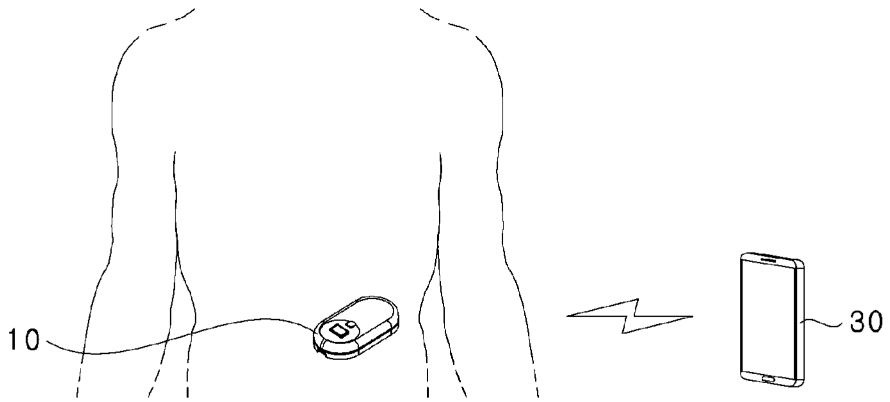
[Fig. 2]
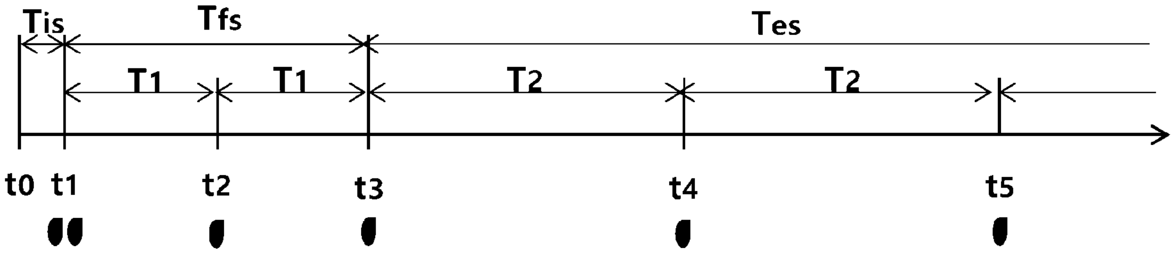
[Fig. 3]
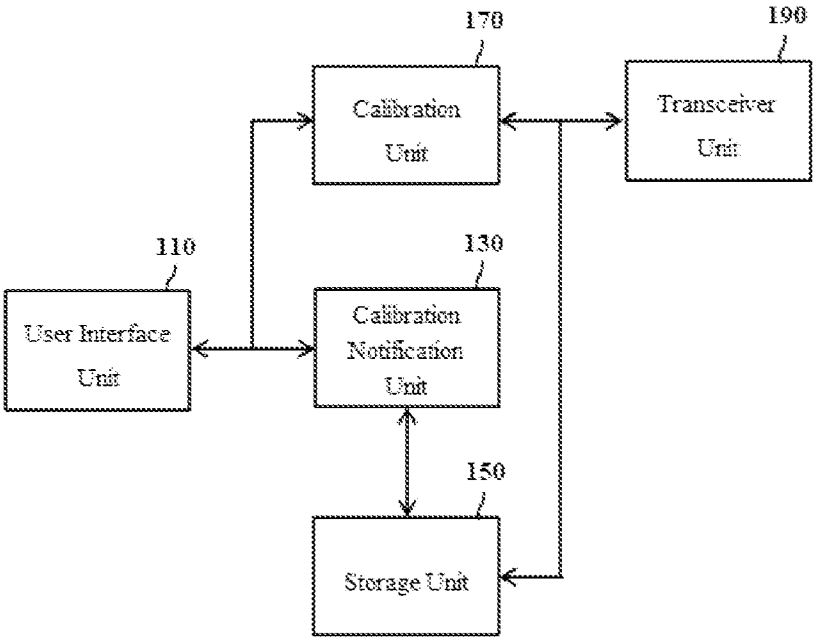

[Fig. 4]
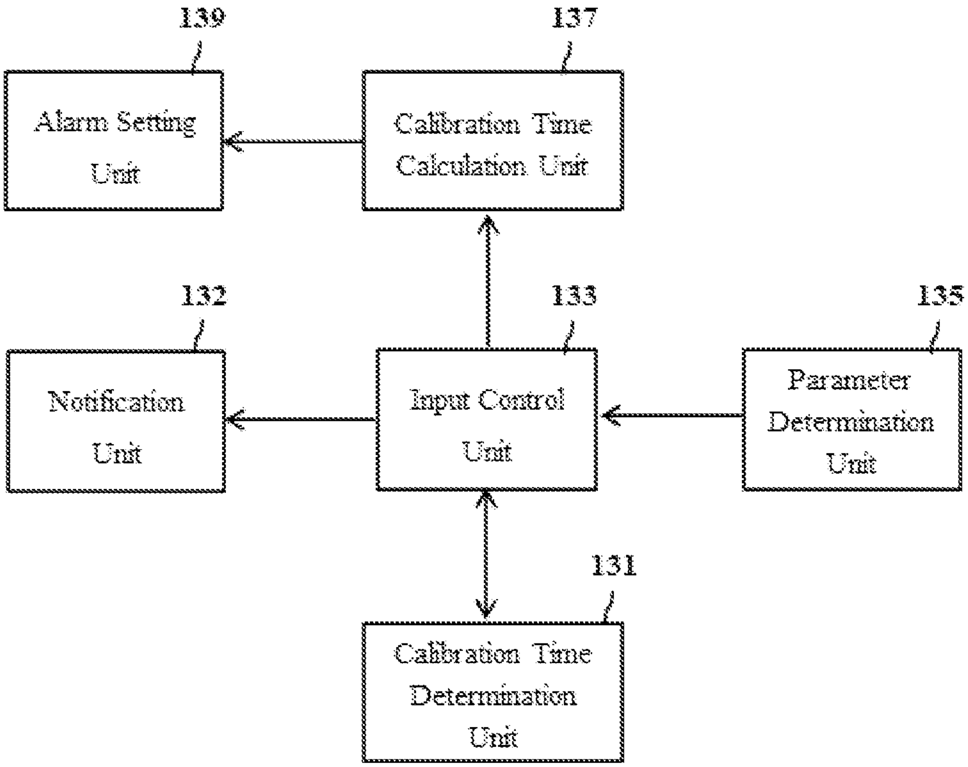

[Fig. 5]
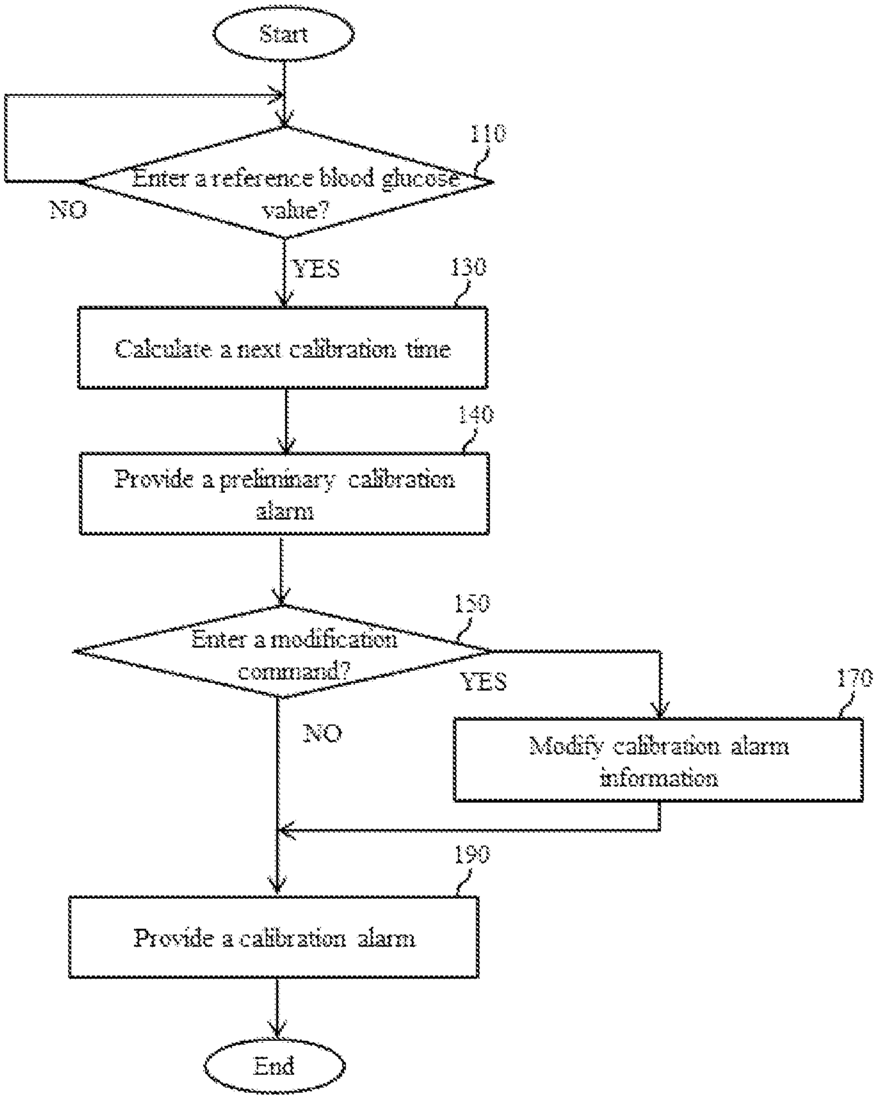
[Fig. 6]
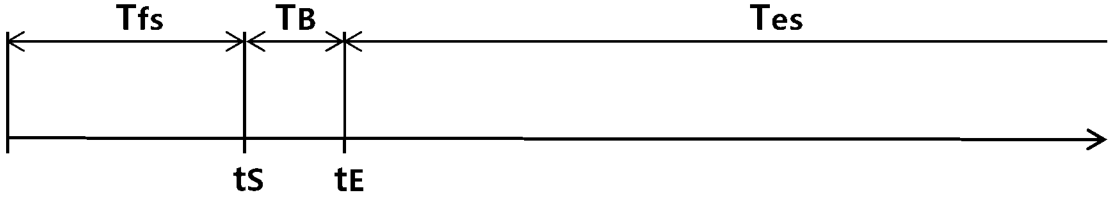

[Fig. 7]
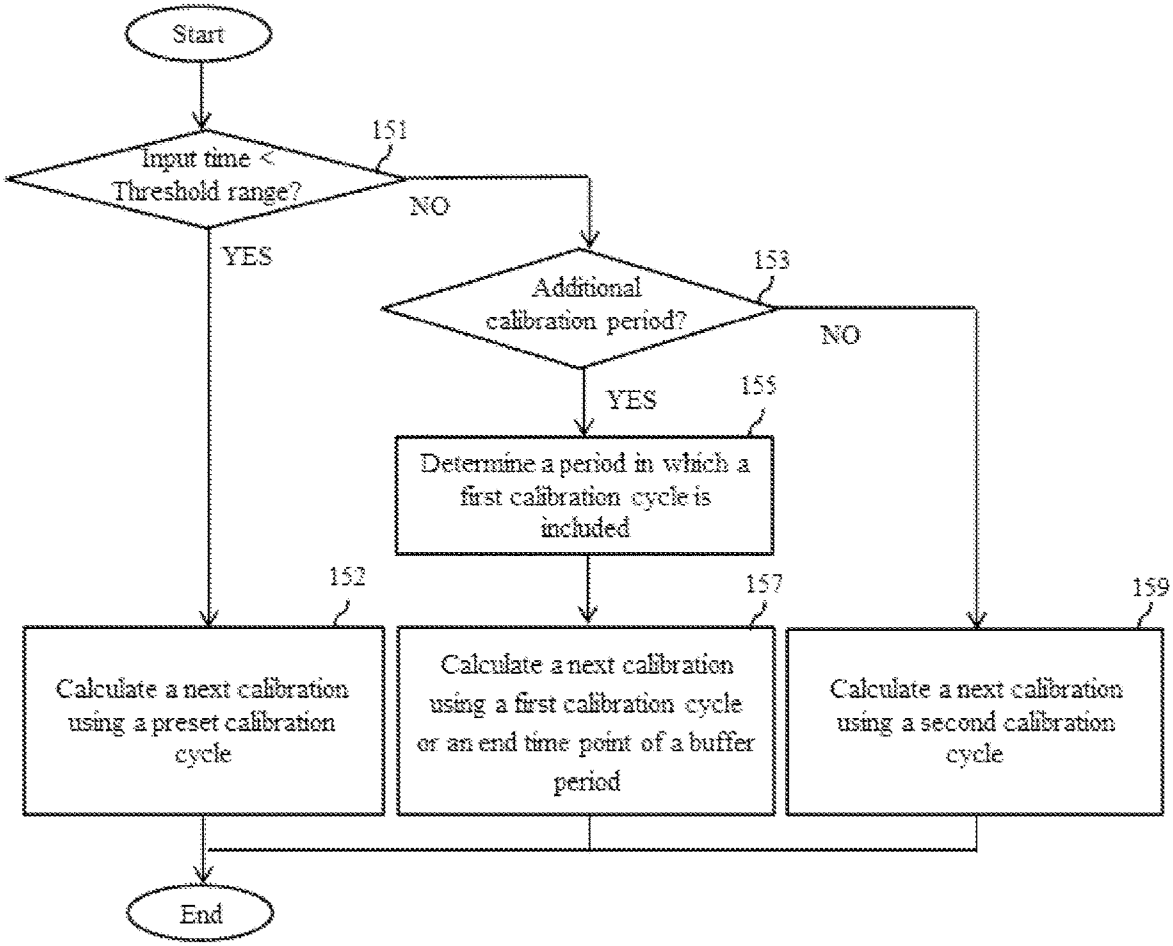

[Fig. 8]
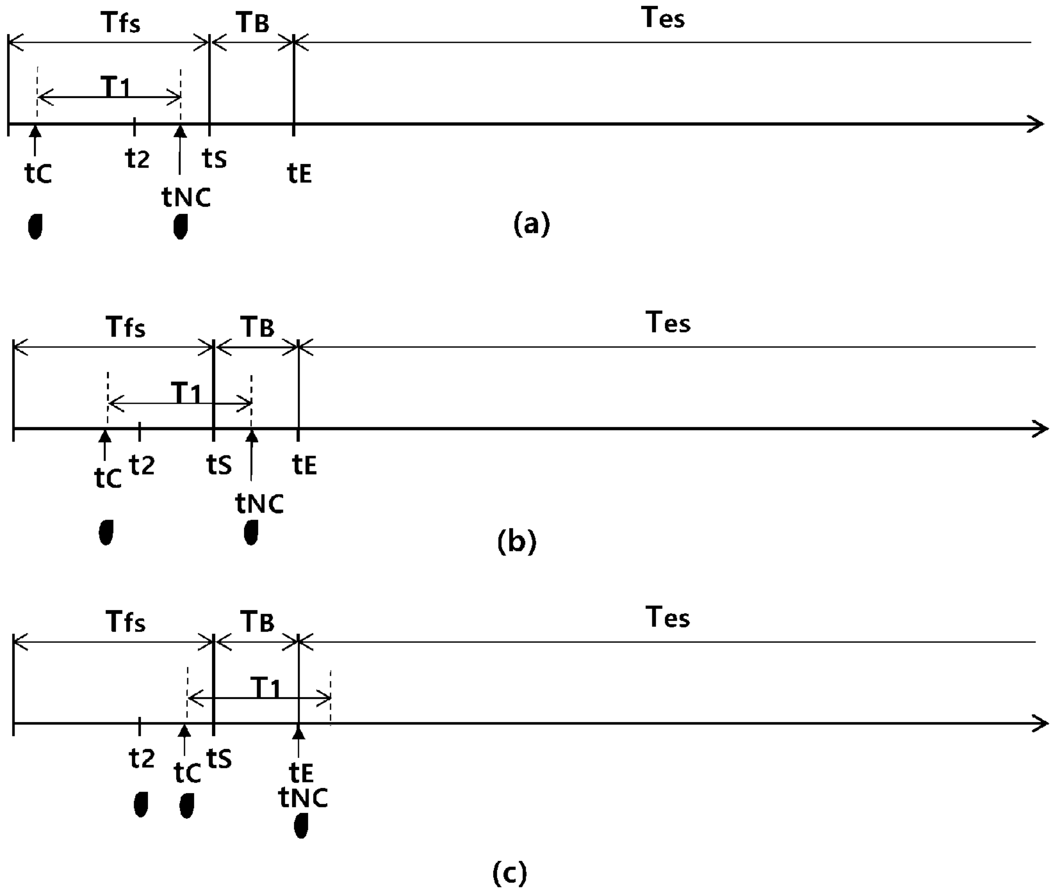
[Fig. 9]
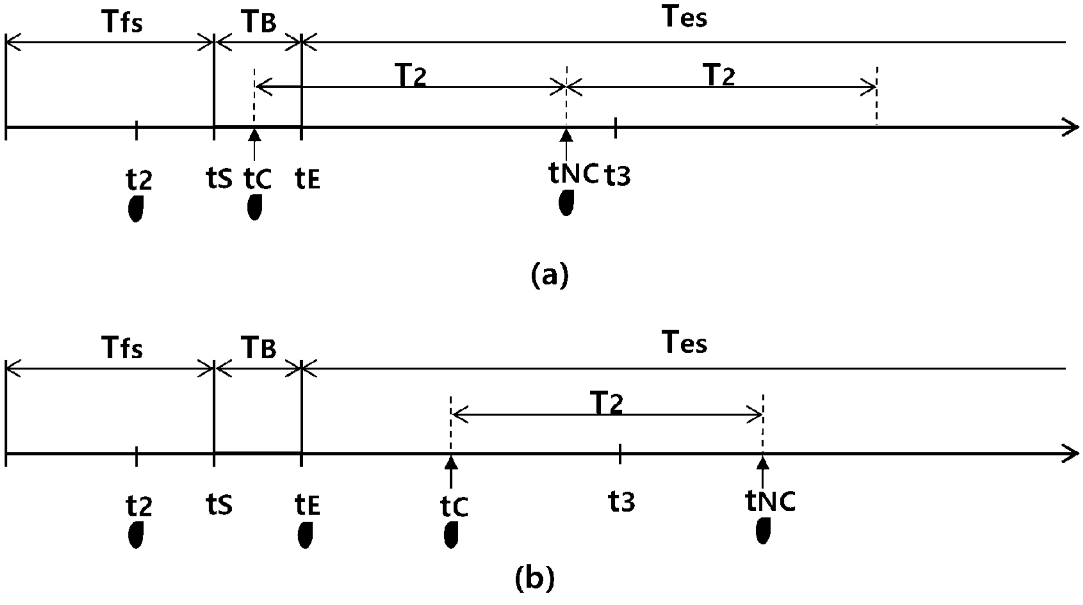

[Fig. 10]
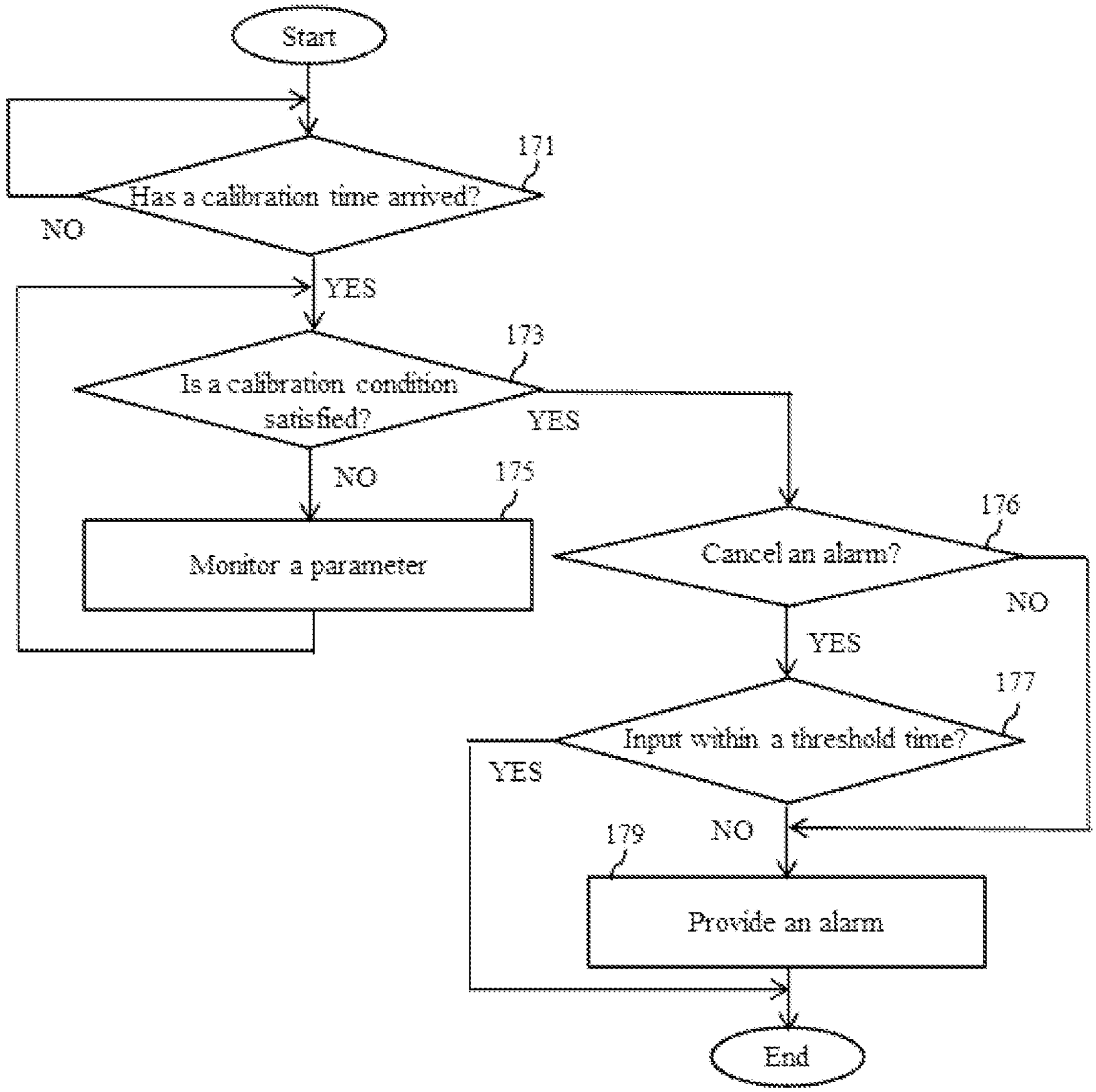

[Fig. 11]
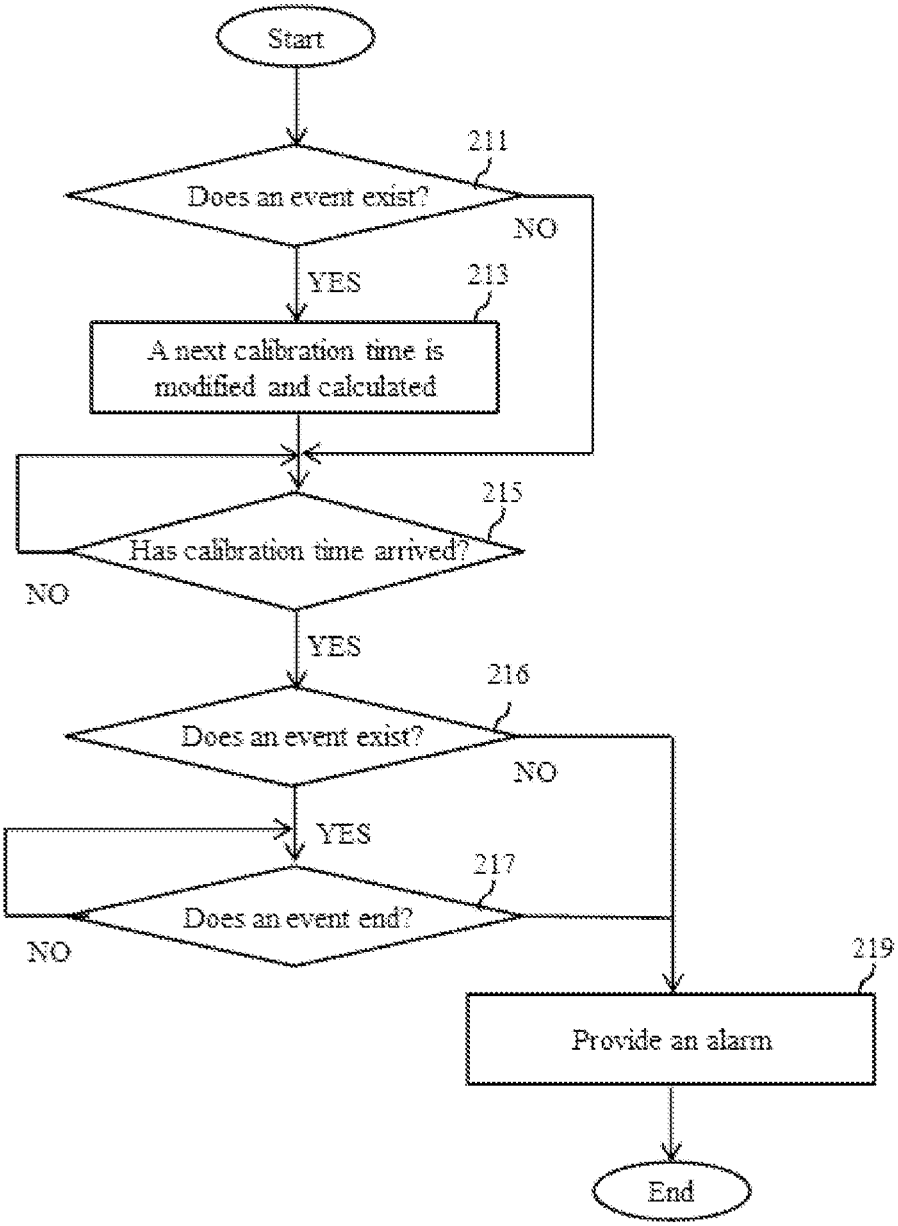

[Fig. 12]
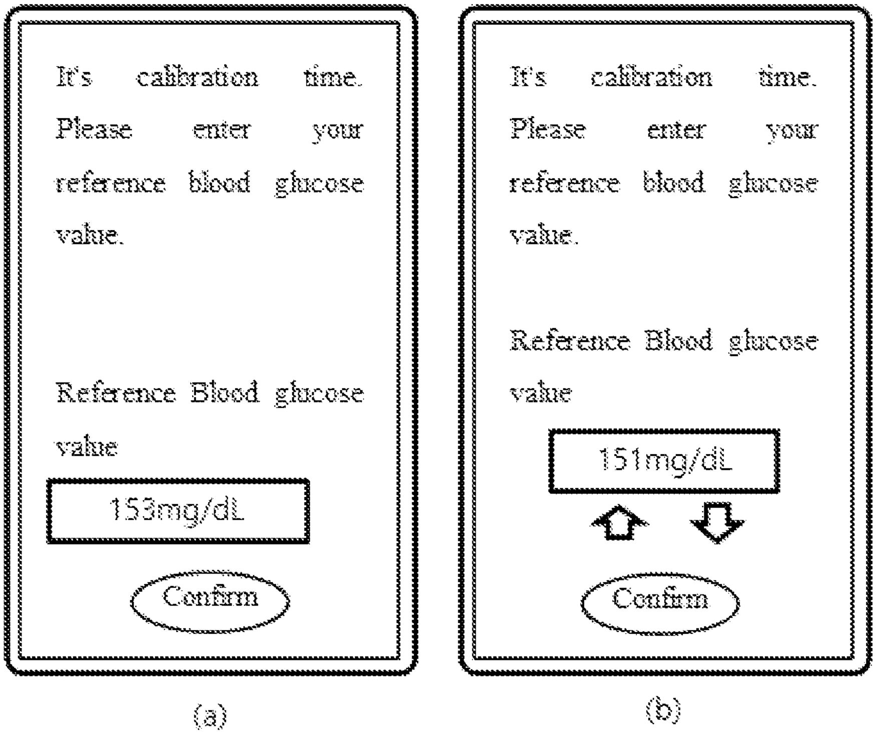
[Fig. 13]
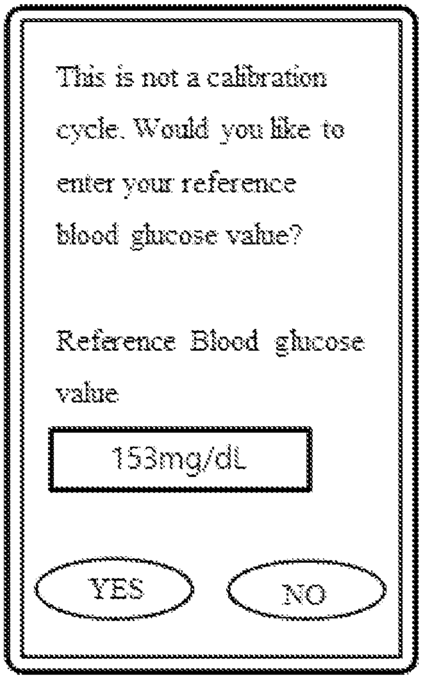

[Fig. 14]
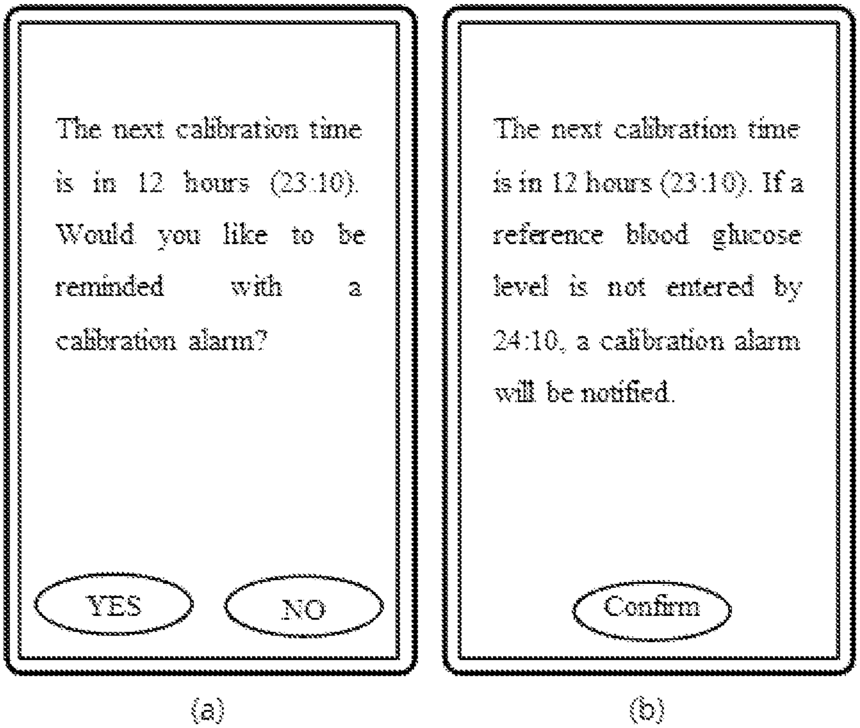
[Fig. 15]
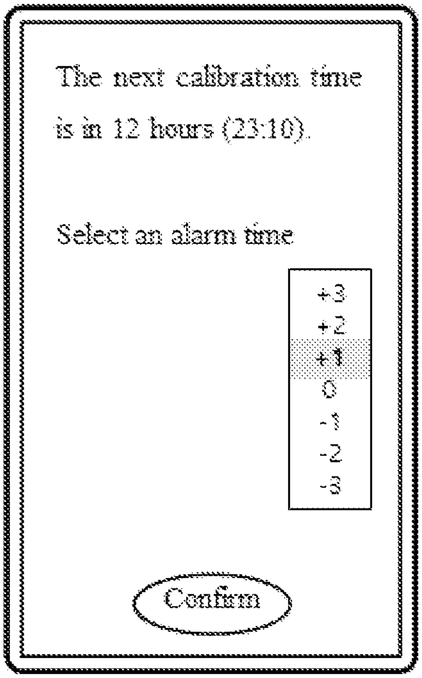

[Fig. 16]
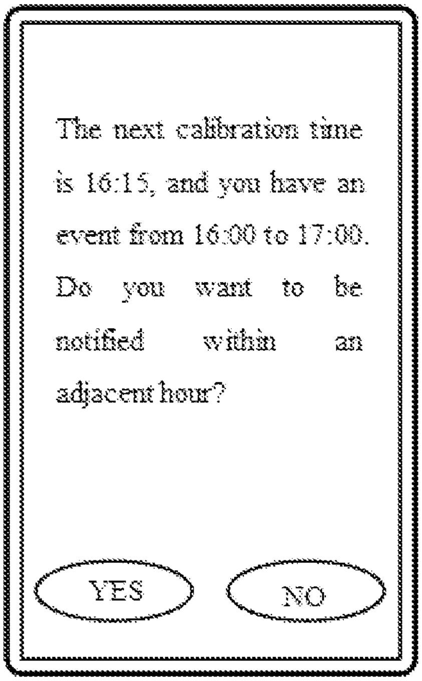

CALIBRATION ALARM METHOD

CROSS-REFERENCE TO RELATED APPLICATIONS

The present application is the U.S. National Phase of PCT Application No. PCT/KR2022/007878 filed on Jun. 2, 2022, which claims the priority to Korean Patent Application No. 10-2021-0194270 filed on Dec. 31, 2021, the entire contents of which are incorporated herein by reference.

TECHNICAL FIELD

The present disclosure relates to a method of providing a calibration alarm in a continuous biometric information measurement system, and more specifically, related to a calibration alarm method which calculates a next calibration time based on the actual calibration time of a user and then informs a user of the next calibration time by calculating the next calibration time based on the actual calibration time even if calibration is performed differently from the preset calibration cycle, and in which a user may conveniently input a reference biometric value by providing a calibration alarm according to the situation information of a user in consideration of the situation information of a user.

BACKGROUND

Diabetes is a chronic medical condition that is common in modern people, and in the Republic of Korea, there are 2 million diabetes patients, about 5% of the total population.

Diabetes occurs when the absolute level of the sugar level in blood is high due to the absolute deficiency or relative insufficiency of insulin, produced by the pancreas, caused by various reasons such as obesity, stress, poor eating habits, and inherited hereditary factors and imbalance regarding glucose in the blood.

The blood usually contains a certain concentration of glucose, and tissue cells gain energy from the glucose.

However, when the glucose is increased excessively more than needed, the glucose cannot be properly stored in the liver, muscle, or adipose tissue and is accumulated in the blood, because of this, patients with diabetes maintain a much higher blood glucose level than normal people, and as excessive blood glucose passes through the tissues and is discharged into the urine, it results in deficiency of glucose, which is absolutely necessary for all tissues of the body, thereby causing abnormalities in respective body tissues.

Diabetes is characterized by substantial absence of subjective symptoms at the beginning of the condition, when diabetes progresses, diabetes-specific symptoms such as overdrink, overeat, polyuria, weight loss, weariness, skin itchiness, and lower ability of naturally healing on injury on hands and feet are shown, and further progression of diabetes leads to complications such as visual disturbances, hypertension, kidney disease, paralysis, periodontal disease, muscle spasms and neuralgia, as well as gangrene.

In order to diagnose diabetes beforehand and manage to prevent the progression of diabetes into complications associated therewith, systematic blood glucose measurement and treatment should be performed.

Diabetes needs to constantly measure blood glucose for management, so the demand for devices related to blood glucose measurement is steadily increasing. It has been confirmed through various studies that, when diabetic patients strictly control the management of blood glucose, the incidence of complications of diabetes is significantly reduced. Accordingly, it is very important for diabetic patients to measure blood glucose regularly for blood glucose management.

The finger prick method is generally used to manage blood glucose level in diabetic patients, and although such a blood collecting glucose measurement device helps diabetics manage blood glucose level, it is difficult to accurately identify frequently changing blood glucose levels because only the results at the time of measurement appear. In addition, the finger prick method requires blood collection to measure blood glucose levels frequently throughout the day, which poses a significant burden on diabetic patients.

Diabetics patients generally experience hyperglycemia and hypoglycemia, and an emergency may occur in the hypoglycemic conditions. Hypoglycemia occurs when sugar content is not kept for a long time, and the patients may become unconscious or die in the worst case. Accordingly, rapid discovery of the hypoglycemic condition is critically important for diabetics. The blood-gathering-type biometric information measuring device intermittently measuring glucose has limited ability to accurately measure blood glucose levels.

Recently, to overcome such a drawback of the blood-collecting-type biometric information measuring device, continuous glucose monitoring systems (CGMSs) inserted into the human body to measure a blood glucose level every few minutes have been developed, and therefore easily perform the management of diabetics and responses to an emergency situation.

The continuous blood glucose monitoring system includes a sensor transmitter that measures biometric values from body fluids by being attached to the body of a user, and a communication terminal that outputs information about the received biometric values to a user. The sensor transmitter includes a sensor for continuous blood glucose measurement that is partially inserted into the human body, and the sensor is inserted into the human body for a certain period of use, for example, approximately 15 days. The sensor transmitter periodically measures biometric values from body fluids, and a biometric management application is installed in the communication terminal to periodically receive biometric values from the sensor transmitter and output the information about the received biometric values to a user.

The sensor of the sensor transmitter is continuously inserted into the skin throughout the usage period, and the sensitivity of the sensor may vary depending on the part of the body where the sensor is inserted, and even if the sensor insertion location on the body part is the same, the sensitivity of the sensor may change over time. Biometric values measured by a sensor transmitter have errors according to changes in sensitivity, and the biometric values of a user must be calibrated by applying calibration factor to the measured biometric values to overcome the errors.

In order to provide accurate biometric values to a user, the biometric values received from the sensor transmitter must be initially calibrated and then continuously calibrated at certain calibration intervals during the usage period of the sensor transmitter. More specifically, during initial calibration, the initial calibration factor is calculated from the reference biometric value measured through a separate measuring device, such as a blood-collecting glucose measurement device, and the biometric value received from the sensor transmitter, and then the received biometric values are calibrated by applying an initial calibration factor to the received biometric values.

During the usage period of the sensor transmitter, the calibration factor is calculated from the reference biometric values measured by a separate measuring device and the biometric values received from the sensor transmitter at each calibration cycle, and the received biometric values must be calibrated by applying the calibration factor until the next calibration cycle arrives.

It takes a certain amount of time for the sensor to stabilize after the sensor is inserted into the body, and in order to accurately measure biometric values before the sensor is stabilized, more frequent calibration is required than after the sensor is stabilized. Therefore, the communication terminal provides a calibration alarm to a user when a set calibration cycle arrives, thereby encouraging a user to input reference biometric values at each set calibration cycle.

However, in a case in which a user inputs the reference biometric values at any time regardless of the set calibration cycle, since calibration alarms are provided to a user again at a preset calibration cycle regardless of the actual input time of the reference biometric value, a user has the problem of repeating unnecessary calibration or receiving unnecessary calibration alarms. On the other hand, in a case in which the calibration cycle is late and the calibration alarm is provided late at night, it may disturb a user or people around him, and in a case in which a user has a schedule such as a meeting or exercise during the calibration cycle, if a calibration alarm is provided to a user regardless of the schedule of a user, there is a problem in that it is difficult for a user to calibrate in a timely manner.

SUMMARY

Technical Problem

As the present disclosure is intended to solve the problems of the conventional calibration alarm method mentioned above, the purpose of the present disclosure is to provide a method of calculating the next calibration time based on the actual calibration time of a user, and providing a calibration alarm to a user based on the calculated next calibration time.

Another purpose of the present disclosure is to provide a method of providing a calibration alarm according to the situation information of a user by considering the situation information of a user (next calibration time, schedule information, etc.).

Another purpose of the present disclosure is to provide a method of providing a calibration alarm that induces a user to enter reference biometric values without missing the calibration cycle by providing a calibration alarm when the reference biometric value is not entered within a threshold time from the set calibration time even if the calibration alarm is canceled according to the situation of a user or the choice of a user.

Another purpose of the present disclosure is to provide a method of providing a calibration alarm that activates the most recent calibrated biometric values on the input screen that is activated to input the reference blood glucose value and allows a user to enter reference biometric values accurately without user error by allowing them to enter reference biometric values based on the activated calibrated biometric values.

Another purpose of the present disclosure is to provide a method of providing a calibration alarm that prevents unnecessary calibration by notifying that the calibration cycle has not arrived when a user command is entered to input reference biometric values regardless of the set calibration cycle, and allows calibration by entering reference biometric values at any time, regardless of the set calibration cycle, as needed.

Solution to Problem

To accomplish the above-described purposes, according to an embodiment of the present disclosure, a calibration alarm method may comprise: inputting a reference biometric value for calibrating a measurement biometric value measured by a sensor; when the reference biometric value is input, calculating a next calibration time based on input time of the reference biometric value; and providing a calibration alarm to a user based on the next calibration time, wherein the sensor is configured to be insertable into body of the user and continuously measure biometric information of the user for a certain period of time.

Here, the sensor may be a sensor configured to measure a blood glucose level of the user, and the reference biometric value may be a reference blood glucose value measured using a blood glucose meter to calibrate a measurement blood glucose value measured by the sensor.

Preferably, the calibration alarm method may further comprise determining whether a notification cancellation command for the calculated next calibration time is received, and wherein if the notification cancellation command is input, a calibration alarm is not provided to the user at the next calibration time.

Preferably, the calibration alarm method may further comprise, if the notification cancellation command is input, comprising determining whether the reference biometric value is input within a preset threshold adjacent time from the next calibration time, wherein if the reference biometric value is not input within the preset threshold adjacent time from the next calibration time, the calibration alarm is provided to the user after the threshold adjacent time has elapsed.

Preferably, the calibration alarm method may further comprise determining whether event information of the user exists at the calculated next calibration time, wherein if the event information of the user exists at the next calibration time, the calibration alarm is not provided to the user at the next calibration time.

The calibration alarm method according to the present disclosure may, if the event information of the user exists at the next calibration time, provide the calibration alarm to the user before or after an event occurs.

Preferably, the calibration alarm method may further comprise: determining whether an adjustment command for adjusting the calculated next calibration time is received; and adjusting the next calibration time based on the adjustment command, wherein the calibration alarm is provided to the user at the adjusted next calibration time.

In the calibration alarm method according to the present disclosure, the reference biometric value may be input by: calculating a calibrated biometric value from a previous calibration factor; outputting the calibrated biometric value to an input field of the reference biometric value together with a calibration alarm message; and adjusting the calibrated biometric value according to an increase or decrease command based on the calibrated biometric value outputted to the input field and inputting the reference biometric value of the next calibration time.

Preferably, the calibration alarm method may further comprise: when an input command of the reference biometric value is input by the user, determining whether input time of the input command is within a threshold time from the next calibration time; if the input time of the input command is out of the threshold time, providing a non-periodic alarm message to the user; and if a reference biometric value is input in response to the non-periodic alarm message, calculating a new calibration factor based on the input reference biometric value, and calibrating the measured biometric value using the new calibration factor.

Preferably, according to an embodiment of the present disclosure, the calculating of the next calibration time may comprise: determining a calibration period to which the input time of the reference biometric value is included; and calculating the next calibration time based on the determined calibration period.

The calibration alarm method according to an embodiment of the present disclosure, if a next reference biometric value is input regardless of the next calibration time, may recalculate the calibration time based on a calibration period in which input time of the next reference biometric value is included.

Advantageous Effects of Invention

The calibration alarm method according to the present disclosure has the following effects.

First, the calibration alarm method according to the present disclosure calculates the next calibration time based on the actual calibration time of a user, so that even if calibration is performed differently from the preset calibration cycle, the next calibration time calculated based on the actual calibration time can be informed to a user.

Second, the calibration alarm method according to the present disclosure takes into account the situation information of a user and provides a calibration alarm according to the situation information of a user, so that a user can conveniently input reference biometric values.

Third, the calibration alarm method according to the present disclosure provides a calibration alarm to a user when the reference biometric value is not entered within a threshold time from the set calibration time even if the calibration alarm is canceled according to the situation of a user or the choice of a user, thereby accurately measuring biometric values by inputting the reference biometric value without missing the calibration cycle.

Fourth, the calibration alarm method according to the present disclosure activates the most recent calibrated biometric value on the input screen activated to input the reference blood glucose value and allows the reference biometric value to be input based on the activated calibrated biometric value, thereby preventing a user from accidentally entering different reference biometric value or incorrectly inputting reference biometric value in the process of directly inputting the reference biometric value.

Fifth, the calibration alarm method according to the present disclosure notifies that the calibration cycle has not arrived when a user command to input a reference biometric value is input regardless of the set calibration cycle, but by allowing the reference biometric value to be entered at any time upon the user request, the reference biometric value may be input at any time regardless of the set calibration cycle as necessary while preventing unnecessary calibration.

BRIEF DESCRIPTION OF THE DRAWINGS

FIG. 1 is a schematic diagram showing a biometric value measurement system according to an embodiment of the present disclosure.

FIG. 2 is a diagram for explaining an example of inputting initial calibration information or periodic calibration information.

FIG. 3 is a functional block diagram for explaining a calibration alarm device according to the present disclosure.

FIG. 4 is a functional block diagram for explaining a calibration notification unit according to the present disclosure.

FIG. 5 is a flowchart for explaining a calibration alarm method according to the present disclosure.

FIG. 6 is a diagram for explaining an example of an entire calibration period used in the calibration alarm method according to the present disclosure.

FIG. 7 is a flowchart illustrating an example of recalculating a next calibration time according to the present disclosure.

FIG. 8 is a diagram illustrating an example of recalculating a next calibration time when an input time of a reference blood glucose value falls within an additional stabilization period.

FIG. 9 is a diagram illustrating an example of recalculating a next calibration time when an input time of a reference blood glucose value does not fall within an additional stabilization period.

FIG. 10 is a diagram for explaining an example of a method for providing a calibration alarm in the present disclosure.

FIG. 11 is a diagram for explaining another example of a method for providing a calibration alarm in the present disclosure.

FIG. 12 shows an example of a calibration alarm provided by a user interface.

FIG. 13 shows another example of a calibration alarm provided by a user interface.

FIG. 14 shows an example of a preliminary calibration alarm provided by a user interface.

FIG. 15 shows another example of a preliminary calibration alarm provided by a user interface.

FIG. 16 shows another example of a preliminary calibration alarm provided by a user interface.

DETAILED DESCRIPTION OF EMBODIMENTS

The technical terms used in the present disclosure, unless specifically defined in a different sense in the present disclosure, should be interpreted as meanings generally understood by those skilled in the art in the technical field to which the present disclosure belongs, and should not be interpreted as an excessively comprehensive sense or an excessively reduced sense. In addition, if the technical term used in the present disclosure is an incorrect technical term that does not accurately express the idea of the present disclosure, it should be replaced with a technical term that can be correctly understood by a person skilled in the art.

Additionally, as used in the present disclosure, singular expressions include plural expressions unless the context clearly dictates otherwise. In the present disclosure, terms such as "consists of" or "comprises" should not be construed as necessarily including all of the various components or steps described in the disclosure and should be interpreted that some of the components or steps may not be included, or additional components or steps may be included.

In addition, it should be noted that the attached drawings are only intended to facilitate easy understanding of the concepts of the present disclosure, and should not be construed as limiting the concepts of the present disclosure by the attached drawings.

Hereinafter, the calibration alarm method according to the present disclosure will be examined in more detail with reference to the attached drawings.

FIG. 1 is a schematic diagram showing a biometric value measurement system according to an embodiment of the present disclosure.

Hereinafter, the blood glucose value will be described as an example of a biometric value, and the reference blood glucose value as an example of a reference biometric value, but various biometric values other than the blood glucose value can be measured depending on the field to which the present disclosure is applied.

Referring to FIG. 1, a biometric value measurement system (1) according to an embodiment of the present disclosure includes a sensor transmitter (10) and a communication terminal (30).

The sensor transmitter (10) is attached to a body, and when the sensor transmitter (10) is attached to the body, one end of the sensor of the sensor transmitter (10) is inserted into a skin and periodically measures a blood glucose signal representing the blood glucose value from the body fluids of a human body.

The communication terminal (30) is a terminal that may receive a blood glucose signal from the sensor transmitter (10), calibrate the received blood glucose signal with a calibration factor, convert the unit into a calibrated blood glucose value, and then display it to a user, so a terminal capable of communicating with the sensor transmitter (10), such as a smartphone, tablet PC, or laptop, may be used. Of course, the communication terminal (30) is not limited thereto, and may be any type of terminal may be used as long as it includes a communication function and a program or application may be installed.

That is, the sensor transmitter (10) generates a blood glucose signal, for example, a current signal, corresponding to the blood glucose value of a user and transmits the blood glucose signal to the communication terminal (30), and the communication terminal (30) calibrates the blood glucose signal of the current value with a calibration factor and converts the unit into a calibrated blood glucose value. Depending on the field to which the present disclosure is applied, the sensor transmitter (10) can directly convert units from a blood glucose signal to a blood glucose value, and the communication terminal (30) can calibrate the blood glucose value received from the sensor transmitter (10) with a calibration factor.

Hereinafter, in the present disclosure, the blood glucose signal or unit-converted blood glucose value measured by the sensor transmitter (10) is referred to as the measured blood glucose value, and the blood glucose value obtained by calibrating the blood glucose signal or unit-converted blood glucose value with a calibration factor in the communication terminal (30) is referred to as the calibrated blood glucose value.

The sensor transmitter (10) transmits information about the measured blood glucose value to the communication terminal (30) at the request of the communication terminal (30) or at a set time, and for data communication between the sensor transmitter (10) and the communication terminal (30), the sensor transmitter (10) and the communication terminal (30) may be connected to each other through a wired communication method such as a USB cable or a wireless communication method such as infrared communication, NFC communication, or Bluetooth.

In case in which communication is connected between the sensor transmitter (10) and the communication terminal (30), the initial calibration factor is calculated using the reference blood glucose value measured by a separate blood glucose meter (not shown) after stabilization of the sensor transmitter (10), and initial calibration is performed on the measured blood glucose value using the initial calibration factor. Thereafter, the communication terminal (30) calibrates the measured blood glucose value received from the sensor transmitter (10) with an initial calibration factor, and provides the calibrated blood glucose value to a user.

In order to accurately calibrate the blood glucose value measured by the sensor transmitter (10), the communication terminal (30) calculates a new calibration factor using the reference blood glucose value measured by a separate blood glucose meter during the usage period of the sensor transmitter (10), and calculates the calibrated blood glucose value by calibrating the measured blood glucose value received from the sensor transmitter using the new calibration factor, and then outputs the calculated calibrated blood glucose value to a user.

FIG. 2 is a diagram to explain an example of inputting initial calibration information and additional calibration information, wherein the calibration information is the reference blood glucose value of a user measured by a test strip through a separate blood glucose meter. Referring to FIG. 2, the sensor transmitter is initially stabilized from the time point when the sensor transmitter and the communication terminal are connected (10) until the set initial stabilization time (TiS) elapses.

At the time when the sensor of the sensor transmitter is initially stabilized (t1), initial calibration information is input to the communication terminal. Here, the initial calibration information may be entered multiple times to accurately calculate the calibration factor. The communication terminal calculates the initial calibration factor using the initial calibration information and the blood glucose value measured by the sensor transmitter, and calculates the calibrated blood glucose value of a user by calibrating the measured blood glucose value received from the sensor transmitter using the initial calibration factor.

After the sensor of the sensor transmitter is initially stabilized, new calibration information is additionally input to the communication terminal preferably at a calibration cycle of 12 hours, 24 hours, etc., until the expiration of the usage period of the sensor transmitter. After the sensor in a sensor transmitter has initially stabilized, the sensor may require additional stabilization for a certain period of time, and in the additional stabilization period (Tfs), new calibration information is input at the first calibration cycle (T1) every 12 hours, and after the additional stabilization period, in the final stabilization period (Tes), new calibration information can be input to the sensor of the sensor transmitter at a second calibration cycle (T2) of 24 hours, 48, etc.

When the sensor is manufactured in the same environment and under the same conditions, the sensor has a certain sensitivity change characteristic (sensitivity drift) after insertion into a human body, and based on the sensitivity change characteristic (sensitivity drift), the length of the additional stabilization period or the final stabilization period may be set differently depending on the manufacturing environment of the sensor, or the calibration cycle in the additional stabilization period or the final stabilization period may be set differently.

Whenever new calibration information is input, the communication terminal calculates a new calibration factor to be used from the time when the new calibration information is input, and calculate the calibrated blood glucose value of a user by calibrating the measured blood glucose value received from the sensor transmitter using the new calibration factor.

In order to accurately measure the blood glucose value continuously using a sensor transmitter, a calibration factor must be calculated using the reference blood glucose value during the usage period of the sensor transmitter, and in order to prevent a user from forgetting to input the reference blood glucose value, a calibration alarm can be provided based on a preset calibration cycle, or a calibration alarm can be provided by recalculating the calibration cycle based on the time when the reference blood glucose value is input.

FIG. 3 is a functional block diagram for explaining the calibration alarm device according to the present disclosure.

The calibration alarm device may be implemented in a communication terminal such as a smart terminal that communicates with the sensor transmitter and notifies a user of the calibrated blood glucose value, or may be implemented through a separate receiving device.

Looking more specifically with reference to FIG. 3, in a case in which a user command for inputting a reference blood glucose value is input through a user interface unit (110), a calibration notification unit (130) activates an input screen for inputting the reference blood glucose value on the user interface unit (110), and a user may input the reference blood glucose value through the activated input screen.

Here, the calibration notification unit (130) determines whether the calibration cycle has arrived based on the calibration cycle stored in a storage unit (150), and when the calibration cycle has arrived, a calibration alarm may be provided to a user through the user interface unit (110), and a user inputs the reference blood glucose value based on the calibration alarm. However, depending on the field to which the present disclosure is applied, the reference blood glucose value can be entered at any time during the entire calibration period at the request of a user, regardless of the calibration cycle.

In one embodiment of the present disclosure, the calibration cycle is preset regardless of the actual input time of the reference blood glucose value, and a calibration alarm may be provided based on the preset calibration cycle, but in another embodiment of the present disclosure, when a user inputs the reference blood glucose value regardless of the calibration cycle, the calibration alarm unit (130) may recalculate the next calibration time based on the input time of the reference blood glucose value, and the calibration cycle stored in the storage unit (150) may be recalculated and then updated based on the calibration time. The calibration alarm unit (150) provides a calibration alarm to a user through the user interface unit (110) when the next calibration time arrives based on the updated calibration cycle.

When a reference blood glucose value is input, a calibration unit (170) determines the measured blood glucose value corresponding to the input time of the reference blood glucose value among the measured blood glucose values received through a transceiver unit (190), and generates a calibration pair consisting of a reference blood glucose value and a corresponding measured blood glucose value. The calibration unit (170) calculates a new calibration factor using the calibration pair. The calibration unit (170) calculates the calibrated blood glucose value by calibrating the measured blood glucose value received after the reference blood glucose value is input using a new calibration factor, and provides the calculated calibrated blood glucose value to a user through the user interface unit (110).

Depending on the field to which the present disclosure is applied, the calibration unit (170) may calculate the calibration factor using the current calibration pair consisting of the input reference blood glucose value and the corresponding measured blood glucose value, but in order to calculate the accurate calibration factor, a new calibration factor may be calculated with a regressive method using the current calibration pair and the past calibration pairs.

Preferably, depending on the field to which the present disclosure is applied, at the time when the reference blood glucose value is input through the user interface unit (110), the calibration notification unit (130) may generate a preliminary calibration alarm to inform a user of the next calibration time, and provide the generated preliminary calibration alarm to a user. The user can control to deactivate the calibration alarm at the next calibration time based on the preliminary calibration alarm or input a command to adjust the next calibration time, and accordingly, the calibration notification unit (130) may control the calibration alarm to be deactivated at the next calibration time or provide a calibration alarm at the adjusted next calibration time.

FIG. 4 is a functional block diagram for explaining the calibration notification unit according to the present disclosure.

Looking more specifically with reference to FIG. 4, a calibration time determination unit (131) determines whether the calibration cycle has arrived based on the calibration cycle stored in the storage unit, and provides a notification signal for notifying that the calibration period has arrived to an input control unit (133) when the calibration cycle has arrived.

The input control unit (133) generates a calibration alarm to notify that a calibration cycle has arrived through a notification unit (132) based on the notification signal, and the input control unit (133) activates an input screen on the user interface unit based on a calibration alarm or based on an input command of a reference blood glucose value which is input through the user interface unit regardless of the calibration alarm. A user can input the reference blood glucose value through the activated input screen.

When the reference blood glucose value is input, the alarm setting unit (139) generates a preliminary calibration alarm to inform the next calibration time and outputs the generated preliminary calibration alarm through the user interface unit. In the preliminary calibration alarm, icons are activated to input a user command to select to provide or not provide a calibration alarm at the next calibration time, to input a user command to adjust the next calibration time, or to input a user command to adjust the next calibration time according to an event existing at the next calibration time. According to a user command, the calibration alarm can be canceled so that the calibration alarm is not provided at the next calibration time, or the next calibration time can be adjusted based on user schedule information, or the next calibration time can be adjusted to an adjacent time of the next calibration time, such as 1 hour before, 2 hours before, 1 hour after, 2 hours after the next calibration time, etc.

Preferably, the calibration notification unit according to the present disclosure may further include a parameter determination unit (135), and when the calibration cycle has arrived, the input control unit (133) determines whether calibration condition parameters such as the rate of change of the calibrated blood glucose value or the size of the calibrated blood glucose value satisfy the calibration conditions before or at the same time as providing the calibration alarm to a user. The input control unit (133) may control a calibration alarm to be provided through the notification unit (132) when the calibration condition parameter satisfies the calibration condition.

In one embodiment of the present disclosure, a calibration cycle is preset and a calibration alarm can be provided at each preset calibration cycle, but in another embodiment of the present disclosure, the calibration cycle is recalculated based on the actual time when a reference blood glucose value is input, and a calibration alarm can be provided with the recalculated calibration cycle.

Preferably, the calibration notification unit according to the present disclosure may further include a calibration time calculation unit (137), the calibration time calculation unit (137) recalculates a next calibration time at the first or second calibration cycle based on the input time of a reference blood glucose value. The calibration time determination unit (137) recalculates and then updates the calibration cycle stored in the storage unit based on the calibration time, and the calibration time determination unit (131) determines whether the calibration cycle has arrived based on the updated calibration cycle.

Meanwhile, in a case in which the next calibration cycle is recalculated based on the input time of the reference blood glucose value, the alarm setting unit (139) can generate a preliminary calibration alarm according to the recalculated next calibration time, and the parameter determination unit (135) may determine whether the calibration condition parameter satisfies the calibration condition at the recalculated next calibration time.

FIG. 5 is a flowchart for explaining the calibration alarm method according to the present disclosure.

Looking more specifically with reference to FIG. 5, it is determined whether the reference blood glucose value has been entered (S110).

In a case in which the reference blood glucose value is input, the next calibration time is calculated (S130), and a preliminary calibration alarm is generated based on the next calibration time and provided to a user (S140). Here, the reference blood glucose value can be input in the calibration cycle according to a user command, or can be input at any time in the entire calibration period regardless of the calibration cycle. The next calibration time can be calculated based on a preset calibration cycle, or the next calibration time can be recalculated based on the time when the reference blood glucose value is input.

Here, the entire calibration period may be sequentially divided into an additional stabilization period, a buffer period, and a final stabilization period in chronological order, starting from the time when the initial stabilization is completed, and in a case in which the next calibration time is recalculated based on the time at which the reference blood glucose value was input, the next calibration time may be recalculated based on the calibration period to which the time at which the reference blood glucose value was input belongs. Depending on the field to which the present disclosure is applied, the entire calibration period can be divided into various calibration periods, which fall within the scope of the present disclosure.

In response to the preliminary calibration alarm, it is determined whether the calibration alarm is canceled at the next calibration time or a modification command is input to adjust the next calibration time (S150). In a case in which a modification command is input, based on the modification command of a user, the calibration alarm information of the next calibration time is modified or the calibration alarm information is modified by adjusting the next calibration time (S170).

In a case in which the next calibration time arrives, a calibration alarm is provided to a user based on the modified calibration alarm information (S190).

FIG. 6 is a diagram for explaining an example of the entire calibration period used in the calibration alarm method according to the present disclosure.

As shown in FIG. 6, after the initial stabilization time point (t1), it can be sequentially divided into an additional stabilization period (Tfs), a buffer period (TB), and a final stabilization period (Tes) in chronological order. The additional stabilization period (Tfs) is a period that requires further stabilization of the sensor after the initial stabilization but before the final stabilization period (Tes), and in the additional stabilization period (Tfs), the reference blood glucose value is input and calibrated every first calibration cycle, and in the final stabilization period (Tes), the reference blood glucose value is input and calibrated every second calibration cycle. Here, the first calibration cycle is characterized as being equal to or shorter than the second calibration cycle. In this way, by receiving and calibrating the reference blood glucose value more frequently in the additional stabilization period (Tfs) than in the final stabilization period (Tes), the sensor can accurately calibrate the measured blood glucose value until final stabilization is achieved.

FIG. 7 is a flowchart illustrating an example of recalculating the next calibration time according to the present disclosure.

Looking more specifically with reference to FIG. 7, it is determined whether the input time of the reference blood glucose value is within a threshold range from the preset calibration cycle (S151). If the input time of the reference blood glucose value falls within a threshold range from the preset calibration cycle, a calibration factor is generated using the input reference blood glucose value, and the next calibration time is calculated using the preset calibration cycle (S152).

However, if the input time of the reference blood glucose value is outside a threshold range compared to the preset calibration cycle, it is determined whether the input time of the reference blood glucose value falls within the additional stabilization period (S153). If the input time of the reference blood glucose value is within an additional stabilization period, the first calibration cycle is added to the input time of the reference blood glucose value so as to determine a calibration period to which the first calibration cycle after the input time of the reference blood glucose value belongs (S155). Depending on whether the calibration period to which the first calibration cycle after the input time of the reference blood glucose value belongs is an additional stabilization period, a buffer period, or a final stabilization period, the next calibration time is calculated using the first calibration cycle or the end time point of the buffer period (S157).

However, if the input time of the reference blood glucose value is not in the additional stabilization period, that is, if the input time of the reference blood glucose value belongs to the buffer period or the final stabilization period, the next calibration time is calculated using the second calibration cycle (S159).

Depending on the field to which the present disclosure is applied, the step of determining whether the input time of the reference blood glucose value is within a threshold range from the preset calibration cycle is omitted, and it is determined whether the input time of the reference blood glucose value belongs to any calibration period among the additional stabilization period, buffer period, or final stabilization period, and based on this, the next calibration time may be calculated in the manner described above based on the input time of the reference blood glucose value.

FIG. 8 is a diagram illustrating an example of recalculating the next calibration time in a case in which the input time of the reference blood glucose value falls within the additional stabilization period.

As shown in FIG. 8(*a*), in a case in which the preset first calibration cycle ($T_1$) after the input time of the reference biometric value ($t_C$) falls within the additional stabilization period ($T_{fs}$), the next calibration time ($t_{NC}$) is recalculated using the preset first calibration cycle ($T_1$) after the input time of the reference biometric value ($t_C$).

As shown in FIG. 8(*b*), in a case in which the preset first calibration cycle ($T_1$) after the input time of the reference biometric value ($t_C$) falls within the buffer period ($T_B$), the next calibration time ($t_{NC}$) is recalculated using the preset first calibration cycle ($T_1$) after the input time of the reference biometric value ($t_C$).

As shown in FIG. 8(*c*), in a case in which the preset first calibration cycle ($T_1$) after the input time of the reference biometric value ($t_C$) falls within the final stabilization period ($T_{es}$), the next calibration time ($t_{NC}$) is recalculated using the end time point ($t_E$) of the buffer period.

FIG. 9 is a diagram illustrating an example of recalculating the next calibration time when the input time of the reference blood glucose value does not belong to the additional stabilization period.

As shown in FIG. 9(*a*), when the input time of the reference biometric value ($t_C$) falls within the buffer period ($T_B$), the next calibration time ($t_{NC}$) is recalculated using the preset second calibration cycle ($T_2$) after the input time of the reference biometric value ($t_C$).

As shown in FIG. 9(*b*), when the input time of the reference biometric value ($t_C$) falls within the final stabilization period ($T_{es}$), the next calibration time ($t_{NC}$) is recalculated using the preset second calibration cycle ($T_2$) after the input time of the reference biometric value ($t_C$).

FIG. 10 is a diagram for explaining an example of a method for providing a calibration alarm in the present disclosure.

Looking more specifically with reference to FIG. 10, it is determined whether the calibration time has arrived (S171).

If the calibration time arrives, it is determined whether the calibration condition parameter measured at the time the calibration time arrives satisfies the calibration condition (S173). Here, the calibration condition parameter may be a rate of change of the calibrated blood glucose value, a lower limit threshold value, or an upper limit threshold value. In this way, by determining whether the calibration condition parameter satisfies the calibration condition before or when providing a calibration alarm, it prevents the calibration factor from being calculated using the reference blood glucose value measured at a time when the rate of change of blood glucose value exceeds threshold rate, indicating a rapid rise or fall in the blood glucose value. Or, by determining whether the calibration condition parameter satisfies the calibration condition before or when providing the calibration alarm, it prevents the calibration factor from being calculated using the reference blood glucose value measured at the time when the blood glucose value exceeds the lower or upper threshold value.

If the calibration condition parameter measured at the time when the calibration time arrives does not satisfy the calibration condition, the calibration condition parameter is monitored for a certain period of time after the calibration time (S175) to determine whether the calibration condition parameter satisfies the calibration condition within a certain period of time. If the calibration condition parameter does not satisfy the calibration condition after a certain period of time, an error message is generated and the generated error message is provided to a user. Here, the error message may be a message to remove the sensor, a message to calibrate by entering a plurality of reference blood glucose values, or a message that calibration is not possible, depending on the error condition.

Meanwhile, if the calibration condition parameter measured at the time the calibration time arrives satisfies the calibration condition or the calibration condition parameter monitored for a certain period of time satisfies the calibration condition, it is determined whether the calibration alarm of the calibration time is canceled (S176). If the calibration alarm of the calibration time is not canceled, a calibration alarm is generated and the generated calibration alarm is provided to a user (S179).

However, if the calibration alarm of the calibration time is canceled, it is determined whether the reference blood glucose value is input within a threshold time (S177). If the reference blood glucose value is entered within the threshold time from the calibration time, a calibration alarm is not provided.

However, even if the calibration alarm of the calibration time is canceled, if the reference blood glucose value is not input during the threshold time from the calibration time, a calibration alarm is provided to a user to input the reference blood glucose value (S179).

FIG. 11 is a diagram for explaining another example of a method for providing a calibration alarm in the present disclosure.

Looking in more detail with reference to FIG. 11, based on the next calibration time calculated at the time the reference blood glucose value is input, it is determined whether the schedule of a user exists at the next calibration time (S211). If the schedule of a user exists at the next calibration time, the next calibration time is corrected and calculated (S213). The schedule of a user may be registered and stored in the storage unit, where the schedule may be event information such as a meeting, meal, exercise, or sleep, and the next calibration time may be modified before the event starts or after the event ends.

By determining whether the modified next calibration time arrives (S215), if the modified next calibration time arrives, it is determined whether the schedule of a user exists at the time when the modified next calibration time arrives (S216). If the schedule of a user does not exist at the time when the modified next calibration time arrives, a calibration alarm is provided to a user (S219).

However, if the schedule of a user exists at the time the modified next calibration time arrives, the end point of a schedule is determined (S217). Here, the time when the schedule ends can be determined based on schedule information registered in the storage unit or by using additional sensors such as a motion sensor, an activity sensor, and a location information sensor. When the schedule ends, a calibration alarm is provided to a user (S219).

In this way, at the time of generating the preliminary calibration alarm, it is determined whether the schedule of a user exists at the next calibration time, and if the next calibration time actually arrives, before providing the calibration alarm, it determines whether the schedule of a user exists again and then provides the calibration alarm to prevent the schedule of a user from being interrupted by the calibration alarm in advance, and to encourage a user to conveniently input the reference blood glucose value by providing the calibration alarm after the schedule ends.

FIG. 12 shows an example of a calibration alarm provided by a user interface.

As shown in FIG. 12(*a*), the calibration alarm activates a screen for entering the reference blood glucose value along with a message notifying that the calibration cycle arrives, and a user can measure the reference blood glucose value using a separate blood glucose meter and test strips and calculate a calibration factor by entering the measured reference blood glucose value directly into the input screen.

However, in a case in which a user directly inputs the reference blood glucose value like this, when entering the reference blood glucose value, a user may mistakenly input a value that is different from the actual reference blood glucose value as the reference blood glucose value, and in this case, there is a problem in that the measured blood glucose value cannot be accurately calibrated. In addition, when measuring the reference blood glucose value, if the hands of a user are contaminated with sugar, etc., the reference blood glucose value may be measured as a value different from the actual blood glucose value, and in this case, there is a problem in that the measured blood glucose value cannot be accurately calibrated due to the incorrectly measured reference blood glucose value.

To solve this problem, as shown in FIG. 12(*b*), when providing a calibration alarm, the current calibrated blood glucose value (151 mg/dL) calculated based on the blood glucose value measured by the sensor of the sensor transmitter is provided on the input screen. As the current calibrated blood glucose value is a blood glucose value calculated with a calibration factor which is calculated immediately before the current calibration cycle, the value does not significantly deviate from the actual blood glucose value of a user, and a user can start from the current calibrated blood glucose value provided on the input screen and input the reference blood glucose value using an icon (for example, an arrow) to increase or decrease the difference between the measured reference blood glucose value and the current calibrated blood glucose value. In this way, by allowing the reference blood glucose value to be entered based on the current calibrated blood glucose value, it is possible to prevent a user from accidentally entering a different reference blood glucose value, and if the difference between the measured reference blood glucose value and the current calibrated blood glucose value is large, a user can be encouraged to measure the reference blood glucose value again.

FIG. 13 shows another example of a calibration alarm provided by a user interface.

As shown in FIG. 13, when a calibration command for inputting a reference blood glucose value is input through the user interface unit, the input control unit compares the calibration cycle with the time at which the calibration command is input, and if the calibration command is input at a time different from the calibration cycle, a screen for inputting the reference blood glucose value is activated along with a message informing a user that the calibration cycle has not arrived.

In this way, when a calibration command to input a reference blood glucose value is input regardless of the calibration cycle, the reference blood glucose value can be entered at any time regardless of the calibration cycle, but by informing a user that the current calibration cycle has not arrived, a user can be prevented from collecting blood unnecessarily and entering the reference blood glucose value.

FIG. 14 shows an example of a preliminary calibration alarm provided by a user interface.

As shown in FIG. 14(*a*), when providing a preliminary calibration alarm, information about the next calibration time is provided and a user can be asked whether to cancel the calibration alarm at the next calibration time.

As shown in FIG. 14(*b*), when a request is made to cancel the calibration alarm at the next calibration time, if the reference blood glucose value is not input within a threshold time, for example, 1 hour from the next calibration time, a notification message is forcibly provided to a user indicating that a calibration alarm is provided.

FIG. 15 shows another example of a preliminary calibration alarm provided by a user interface.

As shown in FIG. 15, when a preliminary calibration alarm is provided, along with information about the next calibration time, an icon for entering a user command to adjust the next calibration time is activated. A user enters a user command to adjust the next calibration time through the icon, and the next calibration time is adjusted according to the user command entered, and the calibration alarm is activated at the adjusted next calibration time.

FIG. 16 shows another example of a preliminary calibration alarm provided by a user interface.

As shown in FIG. 16, when providing a preliminary calibration alarm, it is determined whether a schedule of a user exists at the next calibration time, and if a schedule exists, a user can be asked whether a calibration alarm will be provided before the start of the schedule or after the end of the schedule.

If a user requests to provide a calibration alarm before the start of the schedule or after the end of the schedule, the next calibration time is modified accordingly and the calibration alarm is activated at the next calibration time.

Meanwhile, the above-described embodiments of the present disclosure can be written as a program that can be executed on a computer, and can be implemented in a general-purpose digital computer that operates the program using a computer-readable recording media.

The computer-readable recording media include storage media such as magnetic storage media (e.g., ROM, floppy disk, hard disk, etc.), optical reading media (e.g., CD-ROM, DVD, etc.), and carrier wave (e.g., transmission via Internet).

Although the present disclosure has been described with reference to the embodiments illustrated in the drawings, this is merely an example, and it will be understood by a person having ordinary skill in the art that various modifications and other equivalent embodiments are possible therefrom. Therefore, the technical protection scope of the present invention should be determined by the technical spirit of the appended claims.

The invention claimed is:

1. A calibration alarm method comprising:

inputting a reference biometric value for calibrating a measurement biometric value measured by a sensor;

when the reference biometric value is input, calculating a next calibration time based on input time of the reference biometric value; and providing a calibration alarm to a user based on the next calibration time, wherein the sensor is configured to be insertable into body of the user and continuously measure biometric information of the user for a certain period of time, wherein a calibration period includes an additional stabilization period, a buffer period, and a final stabilization period, and wherein the calculating of the next calibration time comprises:

if the input time of the reference biometric value falls within the additional stabilization period, calculating the next calibration time as earlier of the input time of the reference biometric value plus a first calibration period or an end time point of the buffer period; and if the input time of the reference biometric value falls within the buffer period or the final stabilization period, calculating the next calibration time by adding a second correction cycle to the input time of the reference biometric value.

2. The calibration alarm method according to claim 1, wherein:

the sensor is a sensor configured to measure a blood glucose level of the user, and the reference biometric value is a reference blood glucose value measured using a blood glucose meter to calibrate a measurement blood glucose value measured by the sensor.

3. The calibration alarm method according to claim 1, further comprising determining whether a notification cancellation command for the calculated next calibration time is received, wherein if the notification cancellation command is input, a calibration alarm is not provided to the user at the next calibration time.

4. The calibration alarm method according to claim 3, further comprising, if the notification cancellation command is input, determining whether the reference biometric value is input within a preset threshold adjacent time from the next calibration time, wherein if the reference biometric value is not input within the preset threshold adjacent time from the next calibration time, the calibration alarm is provided to the user after the threshold adjacent time has elapsed.

5. The calibration alarm method according to claim 1, further comprising determining whether event information of the user exists at the calculated next calibration time, wherein if the event information of the user exists at the next calibration time, the calibration alarm is not provided to the user at the next calibration time.

6. The calibration alarm method according to claim 5, wherein if the event information of the user exists at the next calibration time, the calibration alarm is provided to the user before or after an event occurs.

7. The calibration alarm method according to claim 1, further comprising:

determining whether an adjustment command for adjusting the calculated next calibration time is received; and adjusting the next calibration time based on the adjustment command, wherein the calibration alarm is provided to the user at the adjusted next calibration time.

8. The calibration alarm method according to claim 1, wherein the reference biometric value is input by:

calculating a calibrated biometric value from a previous calibration factor;

outputting the calibrated biometric value to an input field of the reference biometric value together with a calibration alarm message; and adjusting the calibrated biometric value according to an increase or decrease command based on the calibrated biometric value outputted to the input field and inputting the reference biometric value of the next calibration time.

9. The calibration alarm method according to claim 1, further comprising:

when an input command of the reference biometric value is input by the user, determining whether input time of the input command is within a threshold time from the next calibration time;

if the input time of the input command is out of the threshold time, providing a non-periodic alarm message to the user; and if a reference biometric value is input in response to the non-periodic alarm message, calculating a new calibration factor based on the input reference biometric value, and calibrating the measured biometric value using the new calibration factor.

10. The calibration alarm method according to claim 1, wherein if a next reference biometric value is input regardless of the next calibration time, the calibration time is recalculated based on the calibration period in which input time of the next reference biometric value is included.

* * * * *